US010386315B2

(12) United States Patent
Patil et al.

(10) Patent No.: US 10,386,315 B2
(45) Date of Patent: Aug. 20, 2019

(54) DIFFERENTIAL SCANNING CALORIMETRY METHOD AND APPARATUS

(71) Applicant: Malvern Panalytical Inc., Westborough, MA (US)

(72) Inventors: Vishal Patil, Westborough, MA (US); Ronan O'Brian, Westborough, MA (US); Edward A. Esposito, Westborough, MA (US); Ben E. Pattison, Westborough, MA (US)

(73) Assignee: Malvern Panalytical Inc., Westborough, MA (US)

(*) Notice: Subject to any disclaimer, the term of this patent is extended or adjusted under 35 U.S.C. 154(b) by 295 days.

(21) Appl. No.: 15/132,859

(22) Filed: Apr. 19, 2016

(65) Prior Publication Data

US 2017/0299532 A1    Oct. 19, 2017

(51) Int. Cl.
*B01L 3/00* (2006.01)
*B01L 7/00* (2006.01)
*G01N 25/48* (2006.01)

(52) U.S. Cl.
CPC .... *G01N 25/4866* (2013.01); *B01L 3/502784* (2013.01); *G01N 25/4886* (2013.01);
(Continued)

(58) Field of Classification Search
CPC ........... G01N 25/4866; G01N 25/4893; G01N 25/4886; B01L 3/503784; B01L 7/52;
(Continued)

(56) References Cited

U.S. PATENT DOCUMENTS 6,216,302 B1 *  4/2001  Preston .................. D06F 43/00
                                                     134/10
8,334,327 B2 * 12/2012  Kaufman ................ B32B 27/20
                                                     521/92
(Continued)

FOREIGN PATENT DOCUMENTS

JP          6-252115       9/1994
JP          9-143773       6/1997
(Continued)

OTHER PUBLICATIONS

International Search Report and Written Opinion dated Nov. 14, 2017, directed to International Application No. PCT/US2017/028201; 21 pages.
(Continued)

*Primary Examiner* — Justin Seo
*Assistant Examiner* — John M Royston
(74) *Attorney, Agent, or Firm* — Morrison & Foerster LLP

(57) ABSTRACT

A method of determining thermal properties of a sample using differential scanning calorimetry (DSC), the method comprises injecting a first separation fluid, a sample plug, and a second separation fluid into a sample cell. The first separation fluid and the sample plug have a first separation interface, and the sample plug and the second fluid have a second separation interface. The method further comprises injecting a reference fluid into a reference cell, heating the sample cell and reference cell, and determining thermal properties of the sample using DSC analysis.

11 Claims, 6 Drawing Sheets

(52) U.S. Cl.
CPC ............ *G01N 25/4893* (2013.01); *B01L 7/52* (2013.01); *B01L 2300/14* (2013.01); *B01L 2300/1822* (2013.01); *B01L 2300/1827* (2013.01)

(58) Field of Classification Search
CPC ..... B01L 2300/1827; B01L 2300/1822; B01L 2300/14
See application file for complete search history.

(56) References Cited

U.S. PATENT DOCUMENTS

| | | | | |
|---|---|---|---|---|
| 2004/0038426 | A1* | 2/2004 | Manalis | G01N 33/54366 436/514 |
| 2011/0059079 | A1* | 3/2011 | Babuka | A61K 39/39591 424/133.1 |
| 2012/0066781 | A1 | 3/2012 | Weiner et al. | |
| 2015/0160205 | A1 | 6/2015 | Baudenbacher et al. | |
| 2017/0304207 | A1* | 10/2017 | Khan | A61K 9/146 |
| 2017/0307553 | A1* | 10/2017 | Jia | G01K 17/006 |

FOREIGN PATENT DOCUMENTS

| | | |
|---|---|---|
| JP | 10-10509 | 1/1998 |
| JP | 2002 277356 | 9/2002 |
| WO | WO 93/01489 | 1/1993 |
| WO | WO-2010/137212 | 12/2010 |

OTHER PUBLICATIONS (Feb. 8, 2006) "VP-DSC MicroCalorimeter User's Manual," located at <https://ctrstbio.org.uic.edu/manuals/> visited on Nov. 7, 2017. (131 pages).

Partial International Search and Notification to Pay Additional Fees dated Jul. 11, 2017, directed to International Application No. PCT/US2017/028201; 5 pages.

* cited by examiner

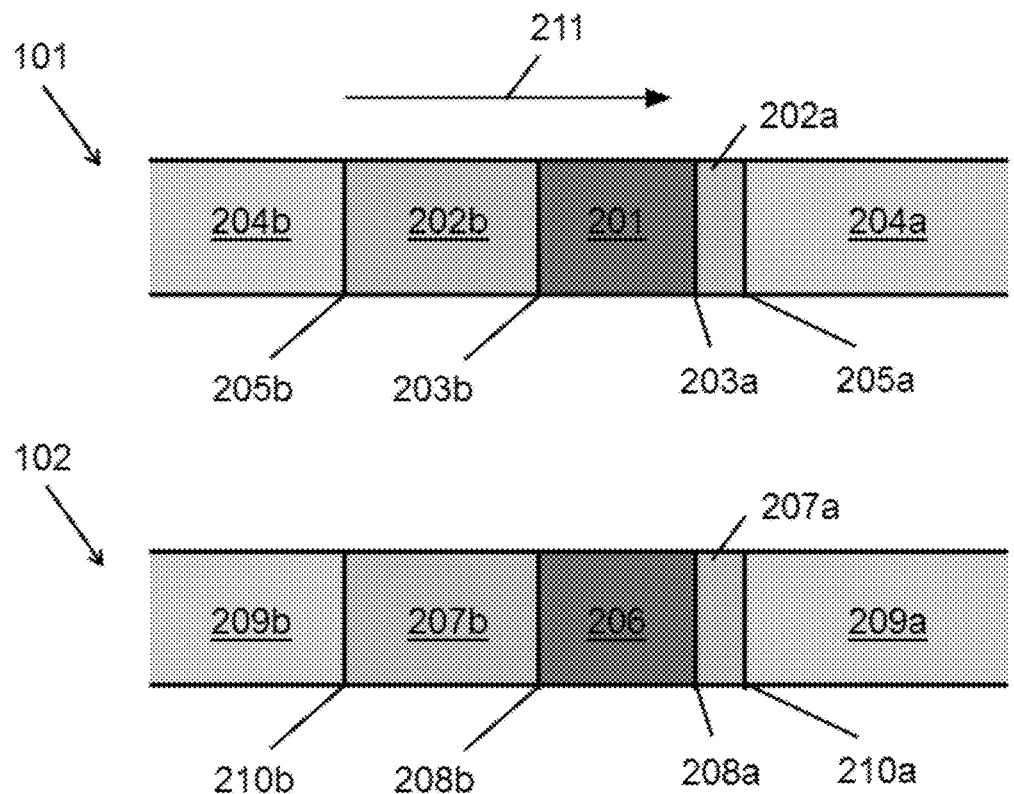
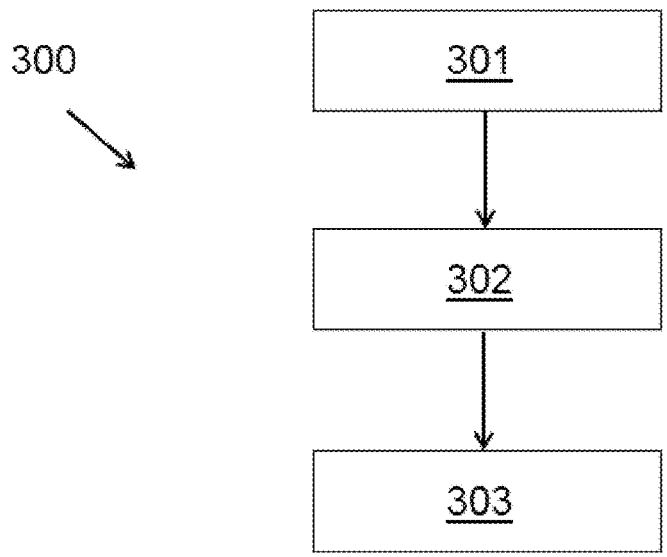
Figure 2
Figure 3

DIFFERENTIAL SCANNING CALORIMETRY METHOD AND APPARATUS

FIELD OF THE INVENTION

The invention relates to a method of performing differential scanning calorimetry, and an apparatus for the same.

BACKGROUND

When preparing medicines containing therapeutic proteins, it is often necessary to know the stability indicators such as melting temperature, and/or heat capacity of the protein solution. A known method for determining such thermal properties of a sample is differential scanning calorimetry (DSC).

A typical capillary DSC system comprises two tubes or cells, one for a sample and one for a reference. Each tube is formed into a coil around a hub. The system heats the two cells using heaters located on the respective hub and monitors the temperature gradient between the sample and reference cells, for example using a Peltier device located between the hubs. The temperature difference can be used to drive a feedback loop which drives the heaters to bring the cells back to equilibrium, or alternatively the system can be left to return to equilibrium passively through conduction. The resulting thermogram of thermal gradient versus temperature of the system can be used, for example, to measure the melting temperature or the heat capacity of the protein solution.

Some protein solutions form a gel when a high concentration sample is heated to a sufficiently high temperature. The gel formation temperature can be used to infer the stability of the protein at lower temperatures. However, this tendency to form a gel has previously made it difficult to analyse high concentration protein samples. The gel blocks the sample cell, and is very hard to clean out once it has formed. The higher the concentration of protein in the protein solution, the more difficult it can be to remove all of the gel.

An existing method for removing a gel from a sample cell is to manually clean with fuming nitric acid. Typically, an operator drops the acid into the sample cell using a pipette, and removes any gel waste that is dislodged by the acid. The process may have to be repeated multiple times until the all of the gel has disintegrated, possibly taking several hours to complete. The fuming nitric acid is a health hazardous solution and even short exposure to it could cause permanent damage to the operator.

As a result of the difficulty of cleaning protein gels from the sample cell, conventional DSC systems are typically limited to measuring protein solutions with protein concentrations in the order of 1 mg/ml. However, as therapeutic protein solutions are formulated at higher and higher protein concentrations, it is necessary to measure thermal properties of protein solutions with much higher concentrations, for example 100 mg/ml and over.

SUMMARY OF THE INVENTION

In accordance with a first aspect of the invention there is provided a method of determining thermal properties of a sample using differential scanning calorimetry (DSC), the method comprising: injecting a first separation fluid, a sample plug, and a second separation fluid into a sample cell, the first separation fluid and the sample plug having a first separation interface, and the sample plug and the second fluid having a second separation interface; injecting a reference fluid into a reference cell; heating the sample cell and reference cell; and determining thermal properties of the sample using DSC analysis.

Using such a method, a small, highly concentrated volume of a sample, such as a protein solution, can be used. The small volume of sample may be easily cleaned from the sample cell, even if it forms a gel. For small volumes of sample, it is necessary to maintain a high concentration of sample in the sample plug to produce a reliably detectable DSC measurement. The first and second separation fluid on either side of the sample plug may counteract hydrodynamic dispersion of the sample, maintaining the concentration of the sample in the sample plug and so allowing DSC measurements to be performed on a small, cleanable volume of sample.

In some embodiments the first separation fluid and the second separation fluid may be immiscible with water. For example, a fluid immiscible with water may be one which maintains an interface between the fluid and water without forming a solution at the interface. In particular for the present invention, a fluid immiscible with water may be a fluid which maintains the first or second separation interface with a sample plug that comprises an aqueous solution. Such a separation fluid may substantially maintain the concentration of a sample solution, such as a protein solution, in the sample plug during DSC measurements (e.g. by preventing evaporation).

In some embodiments, the method may further comprise injecting a first carrier fluid and a second carrier fluid into the sample cell, the first carrier fluid having a first carrier interface with the first separation fluid, and the second carrier fluid having a second carrier interface with the second separation fluid. The first and/or second carrier fluid may, for example, be water.

If the sample comprises an aqueous sample solution, such as a protein solution, water is not a suitable separation fluid as it would be miscible with the sample solution, diluting the sample plug. However, DSC systems are usually calibrated for temperature control using water (and may operate in open loop mode, relying on the sample being water to achieve a specific temperature ramp rate). Such embodiments therefore allow the sample cell to be primarily filled with water, matching a system calibration, with a separation fluid separating the water carrier fluid from the sample plug, maintaining the concentration of sample in the sample plug.

In some embodiments, injecting the reference fluid may comprise injecting a third separation fluid, a reference plug, and a fourth separation fluid into the reference cell, the third separation fluid and the reference plug having a third separation interface, and the reference plug and the fourth separation fluid having a fourth separation interface. Alternatively or additionally, the step of injecting the reference fluid may comprise injecting a third carrier fluid and a fourth carrier fluid into the sample cell, the third carrier fluid having a third carrier interface with the third separation fluid, and the fourth carrier fluid having a fourth carrier interface with the fourth separation fluid. Such methods may ensure that the fluids in the reference cell match the fluids in the sample cell as closely as possible.

In some embodiments, at least one of the first, second, third, and fourth separation fluid may be incompressible and/or inert. An incompressible fluid may for example be a fluid with a bulk modulus of at least 0.1 GPa at NIST STP. An inert fluid may for example be a fluid which does not undergo a chemical reaction with the sample cell, sample plug, and/or carrier fluid. The first, second, third, and/or fourth separation fluid may exhibit no thermal phase change at the running conditions of the DSC system.

In some embodiments, at least one of the first, second, third, and fourth separation fluid may be a silicone oil. Any of the separation fluids may be air. Silicone oil may be preferable to air, as it avoids evaporation from the sample plug at an air-liquid interface, and the volumetric heat capacity of silicone oil is more closely matched to the volumetric heat capacity of an aqueous sample solution in the sample plug. Alternatively at least one of the first, second, third, and fourth separation fluid may be a mineral oil, or an alcohol comprising more than three carbon atoms in its molecular carbon chain, such as butanol or pentanol. A mineral oil may be any oil produced from a mineral source, particularly oil produced by distillation of petroleum.

In some embodiments the volume of sample in the sample plug is between 5 µl and 10 µl.

In some embodiments, the sample may comprise an aqueous solution. The concentration of sample in the aqueous solution in such embodiments may be greater than 100 mg/ml.

Some embodiments may further comprise the step of depressurising the sample cell to below the saturation pressure of the carrier fluid after heating the sample cell. The sample cell may be heated as part of the DSC measurement, or may be heated independently of the DSC measurement. In some embodiments the sample cell may be held at a constant temperature whilst the sample cell is depressurised, or may be maintained at a temperature above a set temperature. For example the temperature of the sample cell may be held at or maintained above 110° C. Depressurising the sample cell may comprise rapidly depressurising the sample cell. For example the pressure in the sample cell may be reduced from a high pressure to a low pressure in less than 1 second.

Reducing the pressure in the sample cell to below the saturation pressure of the carrier fluid causes the carrier fluid to boil. The pressure pulses created during this boiling can exert a mechanical force on any residue in the sample cell. For example, if the sample comprised a protein solution that had formed a gel, the pressure pulses from the boiling may produce force to break up the gel, facilitating cleaning of the sample cell.

Additionally, such embodiments may further comprise the steps of re-pressurising the sample cell to above the saturation pressure of the carrier fluid; and again reducing the pressure in the sample cell again to below the saturation pressure of the carrier fluid.

According to a second aspect of the invention there is provided a method of cleaning a differential scanning calorimetry system, the system comprising a fluid in a sample cell, the method comprising reducing the pressure in the sample cell to below the saturation pressure of the fluid.

The method may further comprise heating the sample cell. In some embodiments the sample cell may be held at a constant temperature whilst the sample cell is depressurised, or may be maintained at a temperature above a set temperature. For example the temperature of the sample cell may be held at or maintained above 110° C. Depressurising the sample cell may comprise rapidly depressurising the sample cell. For example the pressure in the sample cell may be reduced from a high pressure to a low pressure in less than 1 second.

Some embodiments may further comprise the steps of re-pressurising the sample cell to above the saturation pressure of the fluid; and again reducing the pressure in the sample cell to below the saturation pressure of the fluid.

In embodiments of either the first aspect or the second aspect, the sample cell may be depressurised from a pressure greater than 50 psia (340 kPa (absolute)) to a pressure below 15 psia (100 kPa (absolute)), or from greater than 70 psia (480 kPa (absolute)) to below 2 psia (14 kPa (absolute)).

According to a third aspect of the invention there is provided a differential scanning calorimetry system comprising: a sample cell in thermal communication with a sample cell heater; a reference cell in thermal communication with a reference cell heater; and a sample injection subsystem in fluid communication with the sample cell and the reference cell, wherein the sample injection subsystem is operable to inject a first separation fluid, a sample plug, and a second separation fluid into a sample cell, the first separation fluid and the sample plug having a first separation interface, and the sample plug and the second fluid having a second separation interface.

In some embodiments the sample injection subsystem may be operable to inject a first carrier fluid and a second carrier fluid into the sample cell, the first carrier fluid having a first carrier interface with the first separation fluid, and the second carrier fluid having a second carrier interface with the second separation fluid.

In some embodiments, the sample injection subsystem may comprise a sample injector, wherein the sample injector is operable to inject a sample plug into the sample cell. The sample injection subsystem may further comprise a separation fluid injector, wherein the separation fluid injector is operable to inject a first and/or second separation fluid into the sample cell.

In some embodiments, the sample injection subsystem may further comprise a fluid input tube, a carrier fluid source, and a switching valve, wherein the fluid input tube is in fluid communication with the carrier fluid source and with the switching valve, the switching valve operable to place the fluid input tube in fluid communication with the sample cell or the reference cell. The separation fluid injector may comprise a first fluidic element in switchable communication with a separation fluid source and with the fluid input tube between the carrier fluid source and the switching valve, the separation fluid injector operable to inject separation fluid from the first fluidic element into a flow of carrier fluid in the fluid input tube. The sample fluid injector may comprise a second fluidic element in switchable communication with a sample source and with the fluid input tube between the separation fluid injector and the switching valve, the sample injector operable to inject sample from the second fluidic element into a flow of separation fluid in the fluid input tube.

The first and/or second fluidic elements may comprise a fixed volume. The first and/or second fluidic elements may comprise a fixed volume loop (e.g. of tubing). The separation fluid injector may be operable to inject at least a portion of separation fluid held in the first fluidic element into the fluid input tube. Similarly, the sample fluid injector may be operable to inject at least a portion of sample held in the second fluidic element into the fluid input tube. The separation fluid injector may comprise one or more valves. The sample fluid injector may comprise one or more valves.

In some embodiments, the system may further comprise a pressure subsystem in fluid communication with the sample cell, the pressure subsystem comprising a first volume at a first pressure, and a second volume at a second pressure, wherein the pressure subsystem is operable to depressurise the sample cell to a pressure below the saturation pressure of the separation fluid and/or the carrier fluid.

The pressure subsystem may be operable to rapidly depressurise the sample cell. For example the pressure in the sample cell may be reduced from a high pressure to a low pressure in less than 1 second. The pressure subsystem may be operable to depressurise the sample cell from a pressure greater than 50 psia (340 kPa (absolute)) to a pressure below 15 psia (100 kPa (absolute)), or from greater than 70 psia (480 kPa (absolute)) to below 2 psia (14 kPa (absolute)).

According to a fourth aspect of the invention there is provided a differential scanning calorimetry system comprising: a sample cell in thermal communication with a sampler cell heater; a reference cell in thermal communication with a reference cell heater; and a pressure subsystem in fluid communication with the sample cell, wherein the pressure subsystem is operable to rapidly decrease the pressure in the sample cell from at least 50 psia (340 kPa (absolute)) to 15 psia (100 kPa (absolute)) or less.

The pressure subsystem may be operable to reduce the pressure in the sample cell from a high pressure to a low pressure in less than 1 second. The pressure subsystem may be operable to depressurise the sample cell from a pressure greater than 70 psia (480 kPa (absolute)) to below 2 psia (14 kPa (absolute)).

DETAILED DESCRIPTION

The invention is described in further detail below by way of example and with reference to the accompanying drawings, in which:

FIG. 2 is a schematic representation of a sample plug in the sample cell and a reference plug in the reference cell;

FIG. 3 is a flow chart illustrating a method of cleaning a DSC system;

Other embodiments are intentionally within the scope of the invention as defined by the appended claims.

Figure 1:
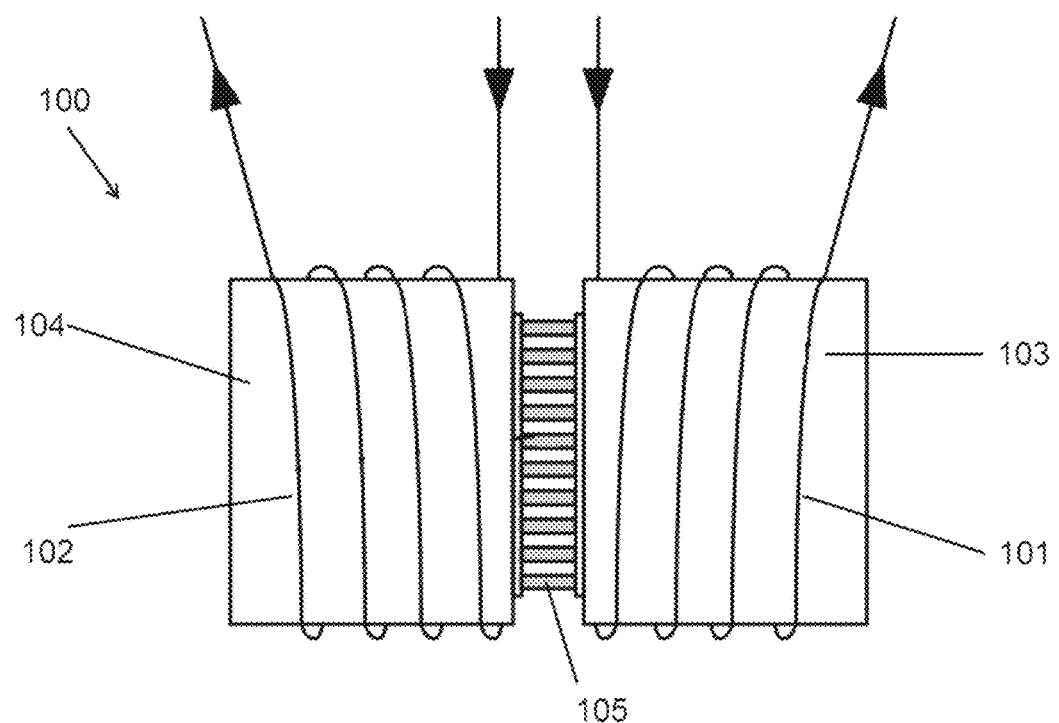
FIG. 1 is a schematic representation of a capillary DSC system.

FIG. 1 illustrates an example capillary DSC system 100 that can be used to measure the thermal properties of a sample, such as a protein solution. The system 100 can be used for example to determine the melting temperature $T_m$ or the heat capacity, $C_p$, of a sample. The system 100 comprises a sample cell 101 and a reference cell 102. Both the sample cell 101 and reference cell 102 comprise a tube wrapped around hubs 103 and 104 respectively. The system 100 heats the two cells 101, 102 using heaters located on the hubs 103, 104 and monitors a temperature gradient between the sample and reference cells using a Peltier device 105 located between the hubs 103, 104. The temperature difference can be used to drive a feedback loop which drives the heaters to bring the cells 101, 102 back to equilibrium. Alternatively the system can be left to return to equilibrium through passively through conduction. The resulting thermogram of thermal gradient versus temperature of the system is used to measure the $T_m$ and $C_p$.

Traditionally DSC systems have been used to measure $T_m$ of protein solutions at dilute protein concentrations in the order of 1 mg/ml. However as therapeutic protein solutions are formulated and delivered at higher and higher concentrations, there is a requirement for measuring $T_m$ at those relevant concentrations to screen molecules and formulation conditions for stability and efficacy.

One issue which arises when working with protein solutions with concentrations in the order of 100 mg/ml is the formation of a solid protein gel when the sample is scanned at high temperatures, at or above $T_m$ of the protein molecule. This protein gel is a porous solid with low permeability to flow which makes it difficult for even aggressive cleaning solutions to reach the gel. To dislodge the solid gel from a coiled or straight capillary, a pressure gradient across the sample cell can be used. However the pressure force required to dislodge or break the gel is proportional to length of the tube occupied by the gel, and inversely proportional to the tube's radius.

When running a thermal scan from 10-110° C. on a high concentration protein sample (Bovine serum albumin (BSA) of concentration 300 mg/ml) in Microcal VP-capillary DSC system (make: Malvern Instruments Inc.), it was found that even a pressure difference in order of 100 psi (690 kPa) across the protein gel was not enough to dislodge the gel. For this reason, it is conventionally recommended that the typical protein concentration in DSC measurements does not to exceed 10 mg/ml.

A current solution to address this issue is to manually clean with fuming nitric acid, as discussed above. In this technique, firstly the DSC system is disconnected from the automated sample handling system. Then the operator, with a pipette, tries to remove as much gel as it is possible to reach from one end of the sample cell, and then drops nitric acid into the tube of the sample cell. The part of the gel accessible to nitric acid gets disintegrated and then the waste products are removed. The process of removing waste fluid and loading nitric acid is repeated multiple times until the complete gel plug is disintegrated. Completion of the process can take hours before all the gel from capillary DSC is removed. Use of fuming nitric acid is also laborious, tedious, and cannot be easily automated. For this reason, capillary DSC systems are generally not used for high concentration protein samples (i.e. with protein concentrations in the order of 100 mg/ml).

FIG. 2 illustrates an example of a method of performing DSC measurements that can be used, for example, to measure high concentration protein samples. FIG. 2 shows a sample plug 201 and a reference plug 206 in the sample cell 101 and reference cell 102 of DSC system 100.

The sample plug 201 comprises a small volume of a sample, such as a protein solution. The sample plug 201 is surrounded circumferentially by the tube of the sample cell 101, and axially by a first separation fluid 202a in front of the sample plug 201 in the direction of flow (indicated by arrow 211), and a second separation fluid 202b behind the sample plug 201 in the direction of flow. The interface between the sample plug 201 and the first separation fluid 202a defines a first separation interface 203a. The interface between the sample plug 201 and the second separation fluid 202b defines a second separation interface 203a. In other words, the sample plug 201 is sandwiched between the first separation fluid 202a and the second separation fluid 202b. The volume of the first separation fluid 202a may be the same as the volume of the second separation fluid 202b, or, as in the illustrated case, may be different.

Typically, the first separation fluid 202a and the second separation fluid 202b will comprise the same fluid, although in some cases the first separation fluid 202a may be different to the second separation fluid 202b. The separation fluid is preferably immiscible with water. Typically the sample plug may comprise an aqueous sample solution, such as an aqueous protein solution. If the separation fluid is immiscible with water, this may maintain the first and second interfaces 203a, 203b. The sample is therefore held in the sample plug 201, with the first and second separation fluid 202a, 202b counteracting hydrodynamic dispersion of the sample plug 201. Here fluids are considered immiscible if the interface between them remains when transported in a capillary during injection.

This arrangement allows the volume of sample to be reduced. Reducing the volume of a protein sample leads to a smaller protein gel plug, which is easier to break up and clean at the end of a measurement. The signal in a DSC measurement is proportional to the total amount of the sample. Low sample concentrations therefore require a larger volume than higher sample concentrations to produce a detectable signal.

Current capillary DSC systems, such as Malvern Instruments Microcal VP-capillary DSC system, have a measurement volume of approximately 130 μl. Such systems can be used to measure protein solutions of concentration in the order of 1 mg/ml. For higher concentrations of protein solutions (e.g. with protein concentrations in the order of 100 mg/ml) the measurement volume can be reduced, as the magnitude of the signal is proportional to the total amount of the sample. For example the volume of the sample plug can be between 5 μl and 20 μl, and in particular may be 10 μl.

The first and/or second separation fluid 202a, 202b may be incompressible, inert, and may exhibit no thermal phase change at the running conditions of the system 100. The first and/or second separation fluid 202a, 202b may for example be a silicone oil. A silicone oil can be any liquid polymerized siloxane with organic side chains, for example polydimethylsiloxane. The first and/or second separation fluid 202a, 202b may alternatively be air. Using a silicone oil rather than air may be preferable as issues like system compliance and sample evaporation at air-liquid interface are mitigated, and the fluid densities (or volumetric heat capacities) are more closely matched. In particular, the thermal expansion of air during DSC measurements may cause noise in the measured data due to movement of the sample. The appropriate immiscible fluid may be different for a different sample type.

As shown in FIG. 2, the arrangement further comprises a first carrier fluid 204a, and a second carrier fluid 204b. The first carrier fluid 204a is in front of the first separation fluid 202a in the direction of flow (indicated by arrow 211), and the second carrier fluid 204b behind the second separation fluid 202b in the direction of flow. The interface between the first separation fluid 202a and the first carrier fluid 204a defines a first carrier interface 205a. The interface between the second separation fluid 202b and the second carrier fluid 204b defines a second carrier interface 205b. In other words the first separation fluid 202a is sandwiched between the first carrier fluid 204a and the sample plug 201. The second separation fluid 202b is sandwiched between the second carrier fluid 204b and the sample plug 201.

The first and second carrier fluid 204a, 204b may comprise the same fluid. Typically the first and second carrier fluid 204a, 204b may comprise water. In capillary DSC system, tests and calibrations are usually performed with water as the working fluid. If the first and second carrier fluid 204a, 204b was the same fluid as the first and second separation fluid 202a, 202b, for example if all four fluids were silicone oil, then the difference in thermal properties between the silicone oil and the calibration may cause incorrect results to be recorded. This may be avoided by using only a small amount of silicone oil as the separation fluid, and water as the carrier fluid, so that the majority of the fluid in the sample cell comprises water, substantially matching the system calibration.

The same arrangement may be used in the reference cell 102, in order that the reference matches the sample as closely as possible. As shown in FIG. 2, the reference plug 206 is surrounded circumferentially by the tube of the reference cell 102, and axially by a third separation fluid 207a in front of the reference plug 206 in the direction of flow (indicated by arrow 211), and a fourth separation fluid 207b behind the reference plug 206 in the direction of flow. The interface between the reference plug 206 and the third separation fluid 207a defines a third separation interface 208a. The interface between the reference plug 206 and the fourth separation fluid 207b defines a fourth separation interface 208a.

The arrangement further comprises a third carrier fluid 209a, and a fourth carrier fluid 209b. The third carrier fluid 209a is in front of the third separation fluid 207a in the direction of flow (indicated by arrow 211), and the fourth carrier fluid 209b is behind the fourth separation fluid 209b in the direction of flow. The interface between the third separation fluid 207a and the third carrier fluid 209a defines a third carrier interface 210a. The interface between the fourth separation fluid 207b and the fourth carrier fluid 207b defines a fourth carrier interface 210b.

The reference plug 206 may comprise a reference fluid, such as a biological buffer solution. Any of the features described in relation to the fluids in sample cell 101 may also apply to the fluids in reference cell 102.

FIG. 3 illustrates a method 300 of using a capillary DSC system, such as DSC system 100, which may break apart gels formed in the sample cell 100. The method of FIG. 3 may be used in conjunction with the fluid arrangement of FIG. 2 (as is shown in FIG. 3), or may be used independently of the fluid arrangement of FIG. 2.

At a first step 301, after DSC measurements have been completed, the sample cell 101 is heated to a high temperature, and the pressure in the sample cell 101 is raised to a high pressure. If the DSC measurements comprised heating the sample cell and increasing the pressure of the sample cell 101, then further heating and increasing of pressure may not be required. The sample cell 101 may be heated to above 100° C., for example to 110° C. The pressure in the sample cell may be raised to greater than 50 psia (340 kPa (absolute)), or greater than 70 psia (480 kPa (absolute)), for example to 74 psia (510 kPa (absolute)).

At a second step 302, the sample cell 101 is rapidly depressurised to below the saturation pressure of a fluid in the sample cell 101, for example to below the saturation pressure of the first and/or second carrier fluid 204a, 204b. For example, the pressure in the sample cell 101 may be reduced from a high pressure to a pressure below the saturation point of a fluid in the sample cell 101 in under 1 second. The pressure may for example be reduced to below 15 psia (100 kPa (absolute)), or to below 2 psia (14 kPa (absolute)), or for example to 1.5 psia (10 kPa (absolute)). During this step, the temperature in the sample cell 101 may be held at an elevated temperature, for example above 100°

C., or for example at 110° C. Heat may for example be provided by a heater on a hub such as hub 103 of system 100.

At an optional step 303, the pressure in the sample cell 101 is again increased to above the saturation point of a fluid in the sample cell 101, and again decreased to below the saturation point of a fluid in the sample cell 101.

Figure 4:
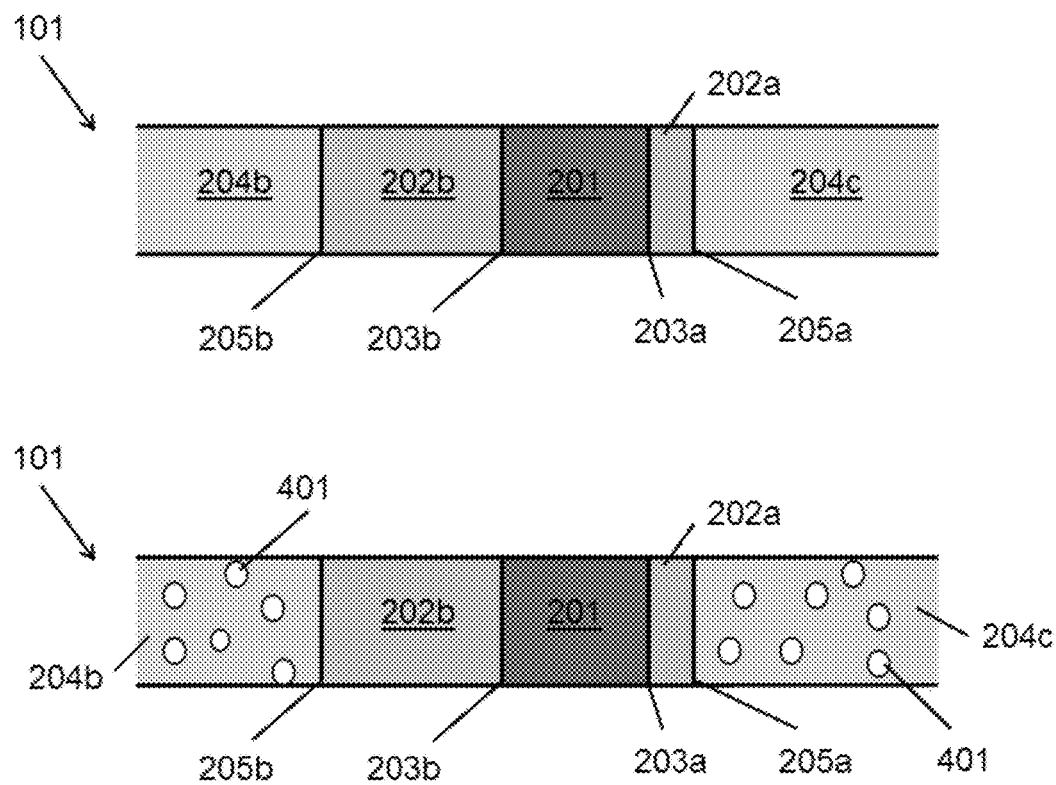
FIG. 4 is a schematic representation of a sample cell before and after depressurisation.

An example of this method is further illustrated in FIG. 4. The tube at the top of FIG. 4 is a representation of the sample cell 101 at a temperature of 110° C. and pressure of 74 psia (510 kPa (absolute)). In these conditions the first and second carrier fluid 204*a*, 204*b*, which may for example be water, is in a superheated state. This may be the condition of the sample cell at the end of a DSC measurement. A sample such as a protein in the sample plug 201 may have formed a gel. In the illustrated example, the sample is surrounded by a first and second separation fluid 202*a*, 202*b* as described above, however this is not necessary.

The tube at the bottom of FIG. 4 is a representation of the sample cell 101 after the pressure has been decreased to 1.5 psia (10 kPa (absolute)). The pressure drop may be produced for example by a vacuum pump. The pressure is below the saturation pressure of the first and second carrier fluid 204*a*, 204*b*, so that these fluids boil, producing bubbles 401 of carrier fluid in the vapour state. As the carrier fluids 204*a*, 204*b* were in a superheated state, and as the sample cell 101 is depressurised rapidly, the carrier fluids 204*a*, 204*b* undergo a fast phase change by undergoing homogeneous and/or heterogeneous boiling. The pressure pulses generated in the boiling process can produce the necessary mechanical disruptive force necessary to break apart the gel formed by the sample, and so aid in cleaning the sample cell 101. The sample cell 101 can be pressurised and depressurised cyclically to produce longer duration of disruptive force inside the DSC system.

The above method described in relation to FIG. 3 or FIG. 4 may equally be applied to the reference cell 102, in order to clean the reference cell 102 after a measurement.

Figure 5:
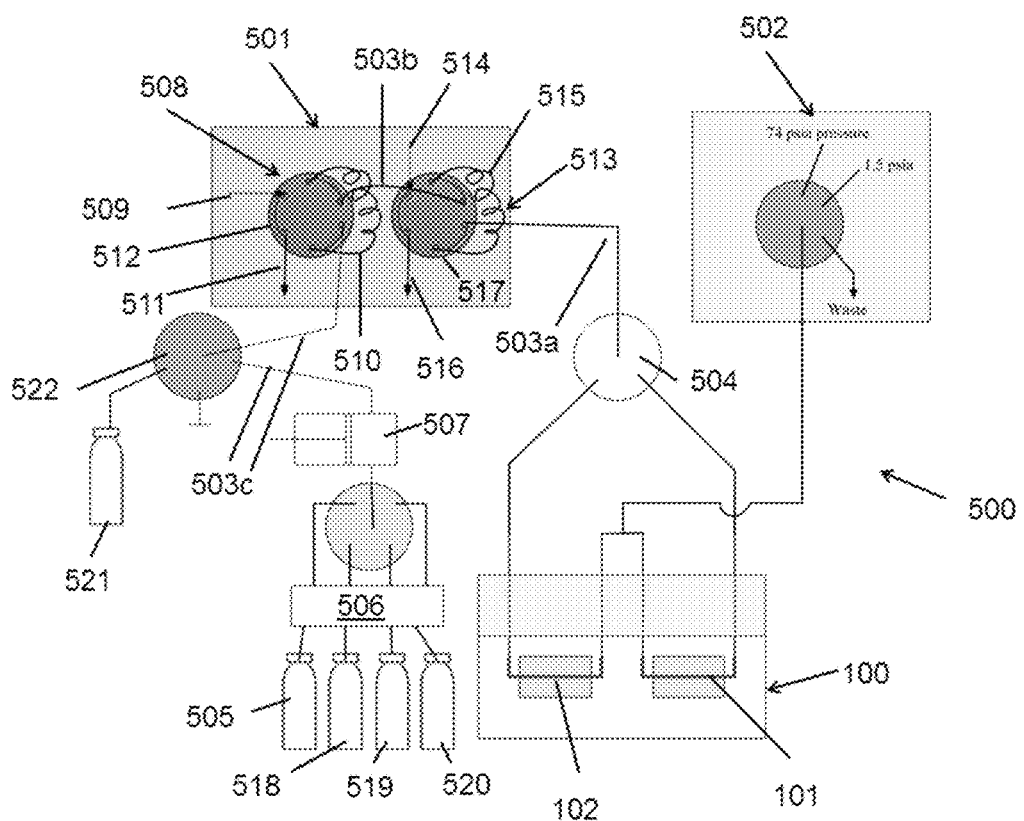
FIG. 5 is a schematic representation of a system for DSC measurements.

FIG. 5 illustrates an example DSC system 500 capable of implementing the methods described above. The system 500 comprises a sample injection subsystem 501 for implementing the arrangement of fluids described in relation to FIG. 2. The system 500 further comprises a pressure subsystem 502 for implementing the methods described in relation to FIG. 3 or 4. Other example DSC systems may comprise an injection subsystem 501 but not a pressure subsystem 502, or may comprise a pressure subsystem 502 but not a sample injection subsystem 501.

The system 500 incorporates the DSC system 100, including the sample cell 101 and reference cell 102 wrapped around hubs 103 and 104 respectively. A fluid input tube comprises three sections: a first section 503*a*, a second section 503*b*, and a third section 503*c*. The first section 503*a* is connected to a two-position switching valve 504. The switching valve 504 is operable to place the fluid input tube in fluid communication with either the sample cell 101 or the reference cell 102. The second section 503*b* is connected within the sample injection subsystem as described below. The third section 503*c* is connected to a carrier fluid source 505 via a vacuum degasser 506 and bidirectional pump 507.

The sample injection subsystem 501 comprises a separation fluid injector 508 and a sample injector 513. The separation fluid injector 508 comprises a separation fluid source 509, a first fluidic element 510, a waste outlet 511, and a first 2-position switching valve 512. In a first position of the first switching valve 512 (not shown in FIG. 5), the separation fluid source 509 is connected to a first end of the first fluidic element 510, and the waste outlet 511 is connected to a second end of the first fluidic element 510. In this position the third section 503*c* of the fluid input tube is connected to the second section 503*b*, so that carrier fluid from the carrier fluid source 505 may flow into the second section 503*b*.

In a second position of the first switching valve 512 (as shown in FIG. 5), the separation fluid source 509 is connected to the waste outlet 511. The third section 503*c* of the fluid input tube is connected to the second end of the first fluidic element 510, and the first end of the first fluidic element 510 is connected to the second section 503*b* of the fluid input tube, so that separation fluid can be pushed from the first fluidic element 510 into the second section 503*b* by the carrier fluid.

The sample injector 513 comprises a sample source 514, a second fluidic element 515, a waste outlet 516, and a second 2-position switching valve 517. In a first position of the second switching valve 517 (not shown in FIG. 5), the sample source 514 is connected to a first end of the second fluidic element 515, and the waste outlet 516 is connected to a second end of the second fluidic element 515. In this position the second section 503*b* of the fluid input tube is connected to the first section 503*a*, so that fluid from the second section 503*a* may flow into the first section 503*a*, and thus into the sample cell 101 or reference cell 102.

In a second position of the second switching valve 517, the sample source 514 is connected to the waste outlet 516. The second section 503*b* of the fluid input tube is connected to the first end of the second fluidic element 515, and the second end of the second fluidic element 515 is connected to the first section 503*a* of the fluid input tube, so that sample can be pushed from the second fluidic element 515 into the second section 503*a*, and thus into the sample cell 101 or reference cell 102, by carrier and/or separation fluid.

In the illustrated example, the first and second fluidic elements 510, 515 are loops of tubing with a fixed volume.

To create the fluid arrangement shown in FIG. 2, initially the first and second switching valves 512, 517 are placed in their first positions, so that the first and second fluidic elements 510, 515 are filled with separation fluid and sample respectively, and carrier fluid flows through to the sample cell 101 or reference cell 102. Then the first switching valve 512 is switched to its second position, so that the first fluidic element 510 is placed in line with the carrier fluid source. At least some of the separation fluid in the first fluidic element 510 may be displaced by the carrier fluid source into the second section 503*b* of the fluid input tube, and through to the first section of the fluid input tube. This process creates a separation fluid plug in the fluid input tube, sandwiched on either side by carrier fluid. All of the fluid in the first fluidic element 510, or only some of the fluid in the first fluidic element 510 may be displaced into the second section 503*b* of the fluid input tube.

Next the second switching valve 517 is switched to its second position, so that the second fluidic element 515 is placed in line with the second section 503*b* of the fluid input tube. The switching valve 517 is switched during the time that the separation fluid is passing from the second section 503*b* to the first section 503*a* of the fluid input tube. At least some of the sample in the second fluidic element 515 is displaced by the separation fluid into the first section 503*a* of the fluid input tube. This process creates a sample plug in the fluid input tube, sandwiched on either side by separation fluid. The amount of sample from the second fluidic element 515 that is displaced into the fluid input tube may controlled in a similar way to the separation fluid. The position of the sample plug within the separation fluid may be controlled. In some embodiments the sample fluid may be substantially central, with equal amounts of separation fluid in front and behind. In other embodiments, the sample fluid may be located off centre in the separation fluid, with more separation fluid in front or behind.

The pressure subsystem 502 is connected to at least one end of the sample cell 101 and reference cell 102. Preferably the pressure 502 subsystem is connected between the sample cell 101 and reference cell 102. The pressure subsystem 502 may comprise, for example, a vacuum pump, or two chambers, one at a high pressure and one at a low pressure. The pressure subsystem 502 may be operable to rapidly switch (e.g. in 1 second or less) the pressure in the sample cell 101 in order to induce a phase change of the carrier fluid, as described above. During pressurisation/depressurisation, the sample injector subsystem 501, or any other elements of the system 500, may be isolated from the sample cell 101 or reference cell 102.

The system 500 may further comprise the following optional elements, which may be used as part of the protocol described below: buffer source 518, solvent source 519 (e.g. comprising IPA), cleaning fluid source 520 (e.g. 20% Contrad® solution), detergent source 521, multi-position selector valve 522.

The protocol for creating and delivering the sandwiched fluid arrangement may be:
Step 1: Load fluidic elements 510, 515 with separation fluid (e.g. silicone oil) and sample;
Step 2: Switch first switching valve 512 into the second position, and dispense approximately 50 µl volume of carrier fluid at 50 µl/min using the pump 507;
Step 3: Switch second switching valve 517 into the second position and dispense approximately 120 µl volume of carrier fluid at 25 µl/min using the pump 507.

The tubing and valves may be cleaned prior to executing the above protocol for creating and delivering the fluids. This may be accomplished as follows:
Switch switching valves 512, 517 into second positions; use the bidirectional pump 517 to flush the tubing and valves with cleaning fluid from the cleaning fluid source 520 (e.g. at 5 ml/min for 2 minutes), followed by washing with solvent from the solvent source 519 (e.g. at 5 ml/min for 4 minutes). Finally water may be used to rinse (e.g. at 5 ml/min for 2 minutes).

For cleaning at the end of measurement, the DSC system may be set to hold the sample and reference cell at 110° C., the inlet to the system may be closed using the multi-position selector valve 522 and the pressure at the outlet of the sample cell 101 switched from a high pressure (e.g. 75 psia or 510 kPa) to a low pressure (e.g. below atmospheric pressure, such as 1.5 psia or 10 kPa) back and forth at least once (e.g. three times). This may be followed by flushing the sample and reference cells with at least one of detergent, cleaning fluids and solvents (e.g. 8M Urea and 2% sodium dodecyl sulfate, SDS) from the detergent source 521 for cleaning it substantially free of protein.

Example dimensions of elements of system 500 may be found in table 1 below. The tubing material may be Teflon® FEP (fluorinated ethylene propylene) upstream of the DSC system and PEEK (polyether ether ketone) on the downstream side. The bidirectional pump 507 may for example be a positive displacement pump. The pump 507 may provide at least one of: a precision of 0.5%, a flow rate range of 5 nl/min to 5 ml/min, and a max back pressure of 100 psi. The bore size of the valve used upstream of DSC may be smaller than that used downstream of the DSC (e.g. 0.4 mm upstream and 1 mm downstream).

The material for all the valves and fittings may be PEEK. The separation fluid may be silicone oil such as that produced by Sigma Aldrich (Product number: 378321-250ML). The kinematic viscosity of the oil may be 10 centistokes at 25 degree Celsius. The carrier fluid may be water.

|  | Volume (µl) | I.D. | Length |
|---|---|---|---|
| First fluidic element 510 | 20.2683 | 0.02 in (0.5 mm) | 100 mm |
| Second part 503b of input tube | 40.5366 | 0.02 in (0.5 mm) | 200 mm |
| Second fluidic element 515 | 7.6 | 0.01 in (0.25 mm) | 150 mm |
| First part 503a of input tube | 20.2683 | 0.02 in (0.5 mm) | 100 mm |
| Tube from switching valve 504 to sample cell | 37.4964 | 0.02 in (0.5 mm) | 185 mm |

Figure 6:
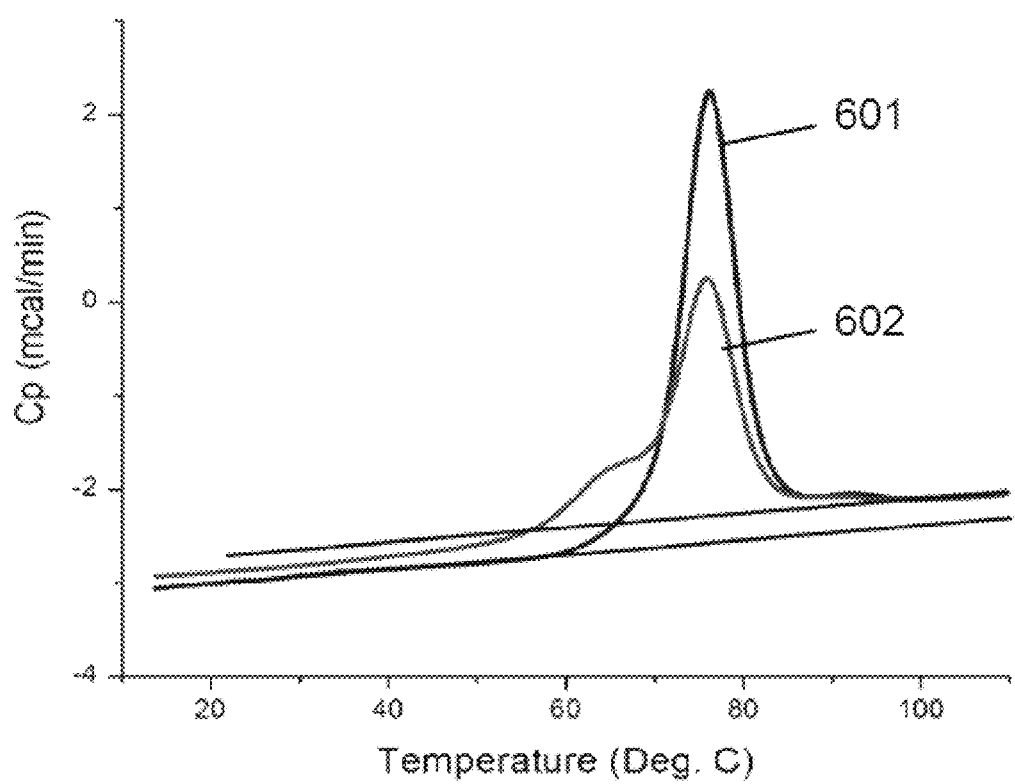
FIG. 6 shows results of an example DSC measurement on a high concentration sample.
Figure 7:
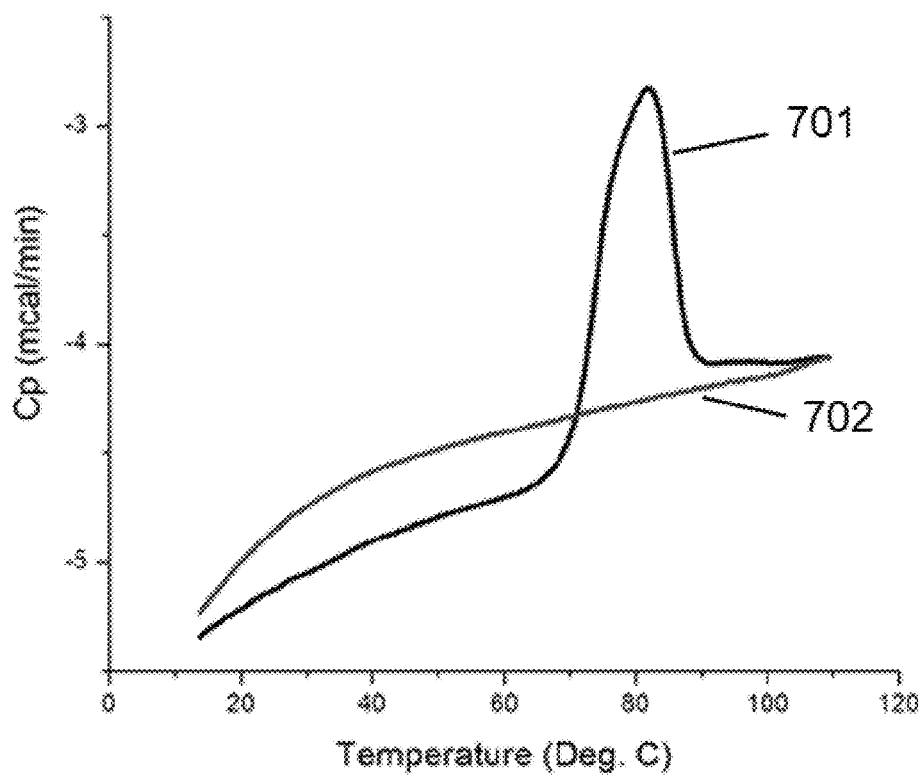
FIG. 7 shows results of another example DSC measurement on a high concentration sample.

FIGS. 6 and 7 show example results of DSC measurements using a system such as system 500. The DSC measurements were performed at set scan rate of 130° C./hr. Gain was set to mid and filter period to 10 s. Two scans on sample delivered to the DSC were performed.

FIG. 6 shows the heat capacity versus temperature for a sample of Lysozyme solution with a concentration of 300 mg/ml for a first DSC scan 601 and a second scan 602. The first DSC scan of the lysozyme shows a transition with a temperature maximum of ~78° C. whereas the second scan has an additional transition with a mid-point temperature of ~62° C. When lysozyme unfolds under these conditions and then is allowed to refold by cooling the sample, some of the protein refolds to the original native state whereas a sub population refolds in to a non-native state due to a cis-trans isomerization of a proline residue. The resulting two populations then give rise to two peaks on the second heating reflecting the stability of these two sub populations The result of a first DSC scan 701 and a second scan 702 obtained from a sample BSA solution with concentration 300 mg/ml of is shown in FIG. 7.

In both measurements, the proteins formed gel particles which were cleaned at the end of the runs leaving the system clog free.

Figure 8:
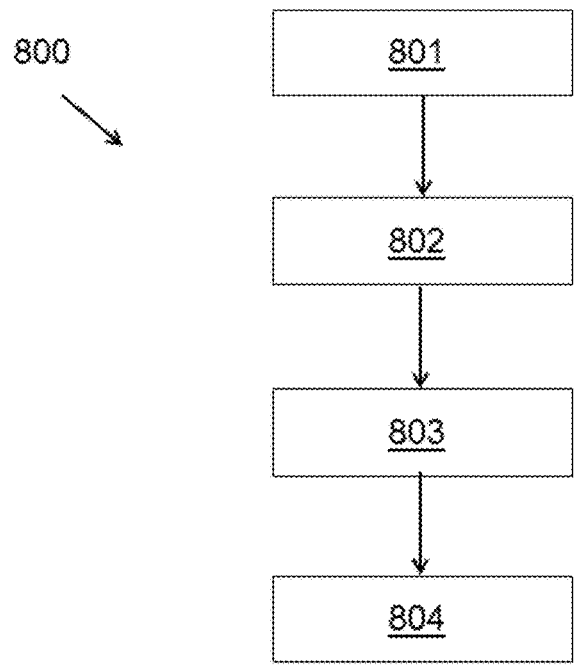
FIG. 8 is a flow chart illustrating a method of performing a DSC measurement.

FIG. 8 illustrates a method 800 of determining thermal properties of a sample using differential scanning calorimetry (DSC), as described above. A first step 801 of the method comprises injecting a first separation fluid, a sample plug, and a second separation fluid into a sample cell, the first separation fluid and the sample plug having a first separation interface, and the sample plug and the second fluid having a second separation interface. In a second step 802, a reference fluid is injected into a reference cell. At a third step 803, the sample cell and reference cell are heated; and at a fourth step 804, thermal properties of the sample are determined using DSC analysis.

Other embodiments are intentionally within the scope of the invention as defined by the appended claims.

The invention claimed is:

1. A method of determining thermal properties of a sample using differential scanning calorimetry (DSC), the method comprising:
    injecting a first separation fluid, a sample plug, and a second separation fluid into a sample cell, the first separation fluid and the sample plug having a first separation interface, and the sample plug and the second fluid having a second separation interface;

injecting a reference fluid into a reference cell;
heating the sample cell and reference cell; and
determining thermal properties of the sample using DSC analysis,
wherein the first separation fluid and the second separation fluid are liquids.

2. The method of claim 1, wherein the first separation fluid and the second separation fluid are immiscible with water.

3. The method of claim 1, comprising injecting a first carrier fluid and a second carrier fluid into the sample cell, the first carrier fluid having a first carrier interface with the first separation fluid, and the second carrier fluid having a second carrier interface with the second separation fluid.

4. The method of claim 1, wherein injecting the reference fluid comprises injecting a third separation fluid, a reference plug, and a fourth separation fluid into the reference cell, the third separation fluid and the reference plug having a third separation interface, and the reference plug and the fourth separation fluid having a fourth separation interface.

5. The method of claim 4, wherein injecting the reference fluid comprises injecting a third carrier fluid and a fourth carrier fluid into the sample cell, the third carrier fluid having a third carrier interface with the third separation fluid, and the fourth carrier fluid having a fourth carrier interface with the fourth separation fluid.

6. The method of claim 5, wherein at least one of the first, second, third, and fourth separation fluid is incompressible and/or inert.

7. The method of claim 5, wherein at least one of the first, second, third, and fourth separation fluid the separation fluid comprises a silicone oil.

8. The method of claim 1, wherein the volume of sample in the sample plug is between 5 µl and 10 µl.

9. The method of claim 1, wherein the sample comprises an aqueous solution, and wherein the concentration of sample in the aqueous solution is greater than 100 mg/ml.

10. The method of claim 3, comprising depressurising the sample cell to below the saturation pressure of the first or second carrier fluid after heating the sample cell.

11. The method of claim 10, comprising re-pressurising the sample cell to above the saturation pressure of the carrier fluid and again reducing the pressure in the sample cell again to below the saturation pressure of the carrier fluid.

* * * * *